US009823175B2

(12) United States Patent
David et al.

(10) Patent No.: US 9,823,175 B2
(45) Date of Patent: Nov. 21, 2017

(54) APPARATUS AND METHOD FOR DETERMINING SOILING OF AN OBJECT (71) Applicant: Duerr Ecoclean GmbH, Filderstadt (DE)

(72) Inventors: Hermann-Josef David, Monschau (DE); Egon Kaeske, Aachen (DE)

(73) Assignee: Duerr Ecoclean GmbH, Filderstadt (DE)

( * ) Notice: Subject to any disclaimer, the term of this patent is extended or adjusted under 35 U.S.C. 154(b) by 1244 days.

(21) Appl. No.: 13/857,005

(22) Filed: Apr. 4, 2013

(65) Prior Publication Data

US 2013/0220371 A1 Aug. 29, 2013

Related U.S. Application Data (63) Continuation of application No. PCT/EP2011/066470, filed on Sep. 21, 2011.

(30) Foreign Application Priority Data

Oct. 4, 2010 (DE) .................... 10 2010 041 930

(51) Int. Cl.
*G01N 1/00* (2006.01)
*G01N 15/06* (2006.01)
(Continued)

(52) U.S. Cl.
CPC ......... *G01N 15/0612* (2013.01); *B08B 3/024* (2013.01); *B08B 3/04* (2013.01);
(Continued)

(58) Field of Classification Search
CPC .. B08B 3/14; B08B 3/024; B08B 3/04; B08B 15/00; G01N 15/02; G01N 15/0205;
(Continued)

(56) References Cited

U.S. PATENT DOCUMENTS 4,559,959 A * 12/1985 Meyers ............... A47L 15/0021
134/109
4,818,414 A * 4/1989 Ross ....................... B01D 24/22
210/104
(Continued)

FOREIGN PATENT DOCUMENTS

DE        698 20 625 T2    11/2004
DE   10 2005 049 227 B4     4/2007
WO       WO 02/099391 A2   12/2002

OTHER PUBLICATIONS

English translation of International Preliminary Report on Patentability of the international searching authority dated Apr. 9, 2013 in international patent application PCT/EP2011/066470 on which the claim of priority is based.

(Continued)

*Primary Examiner* — Benjamin Schmitt
(74) *Attorney, Agent, or Firm* — Walter Ottesen, P.A.

(57) ABSTRACT

An apparatus determines soiling of an object and includes a rinsing zone for rinsing off dirt particles built up on an object with a fluid. A collecting arrangement includes a retaining device for capturing the dirt particles rinsed off from the object and a measuring device measures a physical parameter of the captured dirt particles. A transport system moves the dirt particles captured with the retaining device to the measuring device to permit measuring the physical parameter of the captured dirt particles.

17 Claims, 5 Drawing Sheets (51) Int. Cl.
*B08B 3/02* (2006.01)
*B08B 3/04* (2006.01)
*B08B 3/14* (2006.01)
*G01N 35/00* (2006.01)
*G01N 15/00* (2006.01)
*G01N 1/02* (2006.01)

(52) U.S. Cl.
CPC ............ *B08B 3/14* (2013.01); *G01N 35/0099* (2013.01); *G01N 2001/028* (2013.01); *G01N 2015/0053* (2013.01)

(58) Field of Classification Search
CPC ............ G01N 15/0606; G01N 15/0618; G01N 15/0637; G01N 15/0643; G01N 15/10; G01N 2015/1087; G01N 2015/0019
USPC ..... 134/104.2, 104.3, 104.4; 73/863, 863.71, 73/863.81, 863.91, 864, 864.31
See application file for complete search history.

(56) References Cited

U.S. PATENT DOCUMENTS

| | | |
|---|---|---|
| 5,385,159 A | 1/1995 | Mead |
| 5,502,998 A | 4/1996 | Miller et al. |
| 6,019,110 A | 2/2000 | McClure et al. |
| 2001/0033805 A1* | 10/2001 | Jacobs ................... A61B 1/123 422/3 |
| 2003/0136424 A1 | 7/2003 | Stockert |
| 2003/0142310 A1 | 7/2003 | Bedard et al. |
| 2005/0268948 A1* | 12/2005 | Jeong .................. A47L 15/4204 134/104.4 |
| 2009/0277475 A1 | 11/2009 | Goddard |
| 2011/0311996 A1 | 12/2011 | Friedberger et al. |

OTHER PUBLICATIONS

International Search Report dated Jan. 31, 2012 of international application PCT/EP2011/066470 on which this application is based.

* cited by examiner

APPARATUS AND METHOD FOR DETERMINING SOILING OF AN OBJECT

CROSS REFERENCE TO RELATED APPLICATIONS

This application is a continuation application of international patent application PCT/EP2011/066470, filed Sep. 21, 2011, designating the United States and claiming priority from German application 10 2010 041 930.3, filed Oct. 4, 2010, and the entire content of both applications is incorporated herein by reference.

FIELD OF THE INVENTION

The invention relates to an apparatus for determining soiling of objects, in particular of workpieces, having a rinsing zone for rinsing off dirt, particles built up on an individual object by a fluid, and having a collecting device, which has at least one retaining means for capturing the dirt particles rinsed off from the individual object.

BACKGROUND OF THE INVENTION

Dirt particles, in particular swarf, dust, casting sand or else liquid droplets, may impair the function of industrially produced products, such as for example injection nozzles for internal combustion engines. The cleanliness of workpieces in industrial production processes is therefore of great importance. In industrial production plants, the cleanliness or soiling of workpieces must therefore be systematically examined. Examining cleanliness or soiling is important in particular before intermediate and final assembly operations.

In order to ensure consistent cleanliness of workpieces, it is known to examine their degree of soiling in production processes by means of random samples. For determining the degree of soiling of a workpiece in industrial production, the workpiece is usually rinsed off with liquid by an employee using a spray gun in an analyzing bath. The dirt particles on the workpiece are thereby removed from the workpiece and enter the rinsing liquid. The liquid with the dirt particles is then collected. It is filtered with a filter membrane. Dirt particles from the workpiece are thereby retained in the filter membrane. The filter membrane is subsequently weighed, in order to deduce from the weight of the filter membrane the degree of soiling of the workpiece. Since it is very laborious to examine all of the workpieces in a production process, often only random samples are examined.

However, this manual determination of a degree of soiling of workpieces is not only time-consuming but also imprecise. When the workpiece is rinsed off with liquid, there is the risk of the workpiece being contaminated.

SUMMARY OF THE INVENTION

It is an object of the invention to reliably determine soiling of workpieces in a production process in an automated manner.

This object is achieved by an apparatus of the type mentioned above which includes a transporting device for moving the dirt particles from the individual object that are captured by the at least one retaining means to a measuring device for measuring at least one physical parameter of the dirt particles rinsed off from the individual object.

It is of advantage if the measuring device includes an analyzing device wherein the measuring information concerning the dirt particles rinsed off from the individual object is used to determine the degree of soiling of this object.

In a preferred embodiment of the invention, the retaining means can be displaced by a transporting device in order to move it out of the collecting device into the measuring device. In this case, the retaining means is preferably a filter. This filter may be formed for example as a filter membrane which is held in a membrane holder. The apparatus favorably contains a magazine for such membrane holders with filters. It is of advantage to form the transporting device as an automatically controlled manipulator, in particular as a robot. With this manipulator or robot it is possible to move the membrane holders in an automated manner out of the magazine into the collecting device and from the collecting device into the measuring device.

In a preferred embodiment of the invention, the filter is a portion in a filter belt. This filter belt may be moved from an unwinding station to a winding-up station as a transporting device for the portion in the filter belt.

The apparatus preferably contains a system of lines for circulating fluid for the rinsing off of dirt particles in the rinsing zone. It is of advantage to arrange in the system of lines a suction device for sucking in fluid exposed to dirt particles through the retaining means. A line with one or more nozzles is favorably provided in the rinsing zone for the rinsing off with extraction fluid.

It is of advantage to form the apparatus with a chamber which surrounds the rinsing zone. Then, in order that an object, for example a workpiece, cannot be contaminated when analysing its soiling in the apparatus, and the result of a corresponding soiling analysis cannot be falsified, the apparatus contains a filter, for example a HEPA filter, through which filtered gaseous fluid, for instance air, is fed to the chamber. In a HEPA filter, minute particles with a size to the range of 0.3 µm can be filtered off. A HEPA filter consequently makes it possible in particular to free room air of fine dust, tobacco smoke, fumes, house dust, pollen, blossom dust, pores and odors. With a HEPA filter, overall filtration efficiencies of 99.9% can be achieved for fine dust and suspended matter, that is, of 10,000 dust particles, only 3 are not separated out in a corresponding HEPA filter. A HEPA filter can be constructed with a fine-meshed woven fabric of cellulose, synthetic fibers or glass fibers. This fabric is placed in the filter with up to 1000 layers one on top of the other. As a result, a very great filter area is provided. A particularly good filtering effect can be achieved by the HEPA filter being combined with an activated charcoal filter. This activated charcoal filter is favorably arranged upstream of the HEPA filter. Supplying filtered, gaseous fluid produces a positive pressure in the chamber and in the rinsing zone. This has the consequence that no dust particles, dirt particles and liquid droplets can penetrate into the chamber from outside ambient air. Especially suitable for setting the positive pressure is a fan that admits filtered air to the chamber through the filter. For cleaning the chamber and the rinsing zone, it is practical to equip the apparatus with a device for rinsing walls of the chamber with fluid.

The fact that the rinsing zone with the collecting device and the measuring device are integrated in a container-like transporting cabinet makes it possible for the apparatus to be used flexibly and for it to be easily relocated to different places in an industrial production plant.

It is of advantage to use in particular a microscope with a digital camera and with an evaluation computer as the measuring device in the apparatus. This makes it possible to analyze the degree of soiling, and also the type of soiling, of objects or workpieces by the methods of digital image processing.

In order to determine the soiling of objects, in particular of workpieces, by means of the apparatus according to the invention, it is of advantage first to rinse the chamber in the apparatus in a clean-room atmosphere with extraction fluid. The rinsed-off dirt particles are then collected. In a preferred method for analyzing the soiling, the spatial extent of the collected dirt particles is then compared with a reference value.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
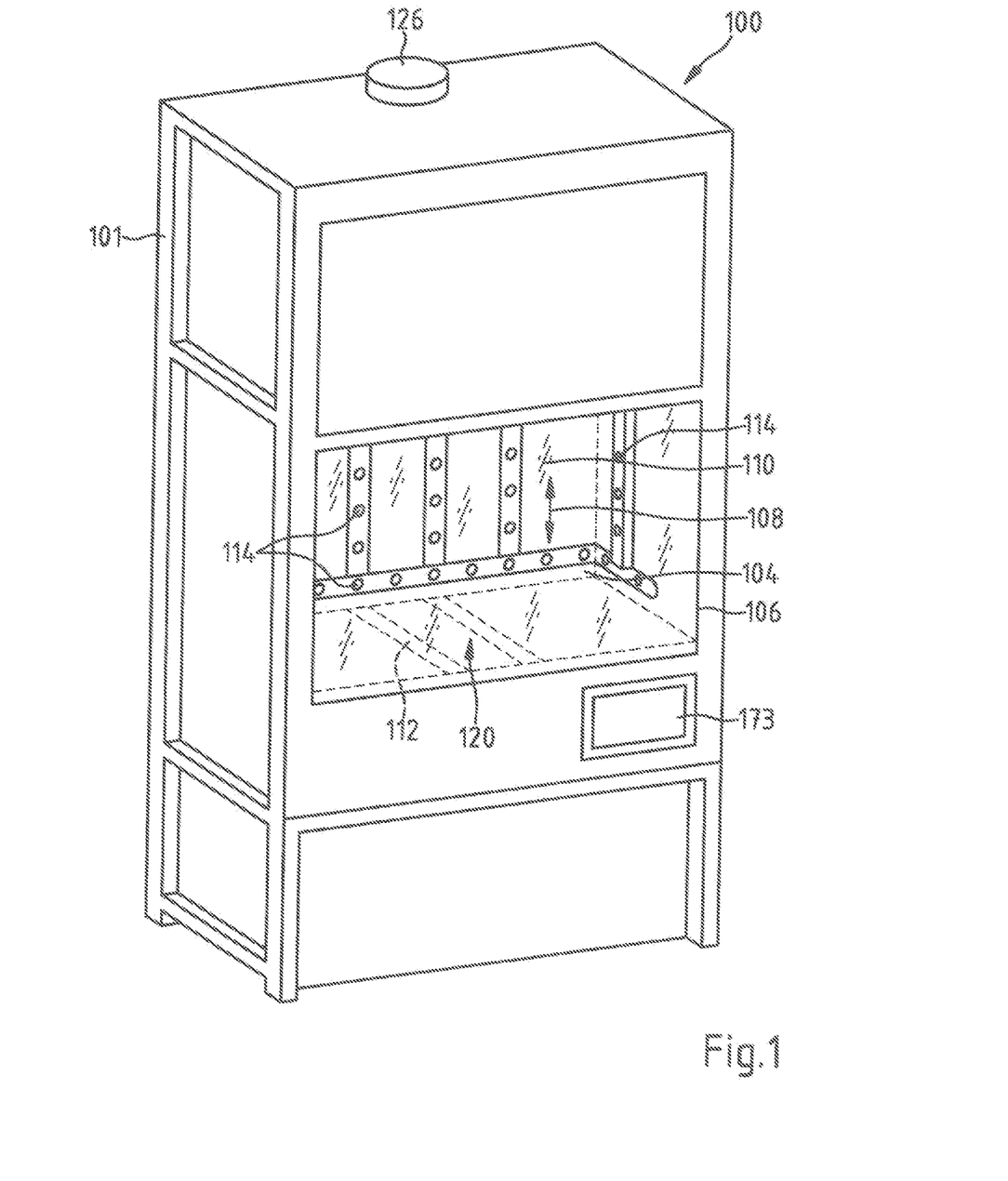
FIG. 1 shows a first apparatus for determining the soiling of workpieces.
Figure 2:
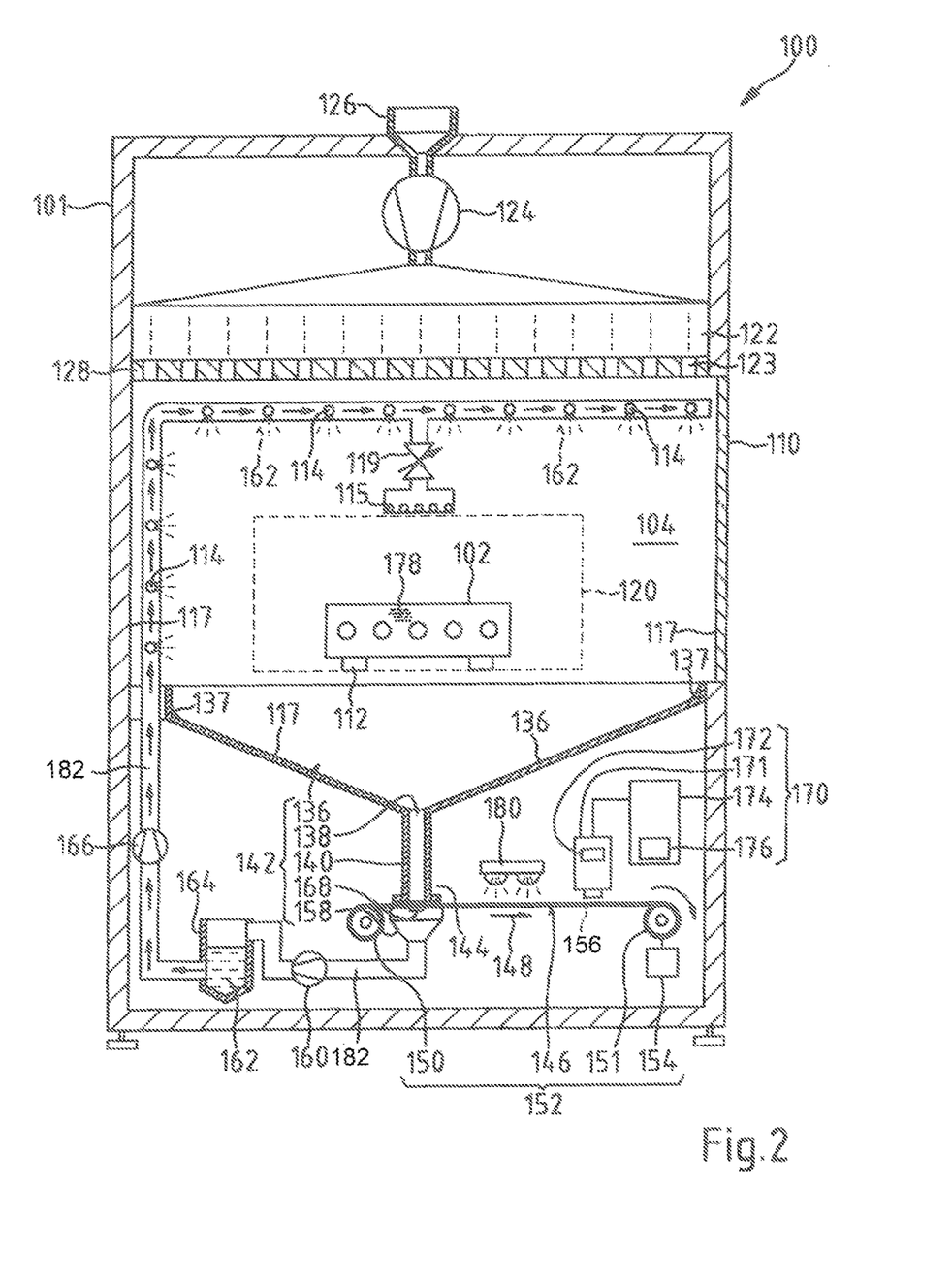
FIG. 2 shows a sectional view of the first apparatus with a collecting device for dirt particles and a measuring device.

FIG. 1 shows an apparatus 100 for determining and analyzing the soiling of workpieces 102 (FIG. 2). The apparatus 100 comprises a container 101 in the form of a transporting cabinet. The container 101 has a chamber 104. For the chamber 104, the container 101 has an access opening 106. The chamber 104 can be opened and closed by means of a glass windowpane 110 that is movable in accordance with the double-headed arrow 108. The chamber 104 contains a holding device 112 for a workpiece, the soiling of which is intended to be analyzed. Spray nozzles 114 are arranged in the chamber 104. The spray nozzles 114 are connected to a system of lines for rinsing liquid as a fluid for rinsing off a workpiece. The spray nozzles 114 make it possible for a workpiece to be rinsed off in the rinsing zone 120 in the chamber 104.

Especially suitable as rinsing liquid for the rinsing off of workpieces is a cleaning liquid in the form of aqueous neutral cleaning agents or cold cleaning agents. With these cleaning liquids, workpieces can be freed of dirt particles and contaminants highly efficiently if the pressure in the system of lines for rinsing liquid in the region of the spray nozzles 114 lies between 1 bar and 6 bar. The spray nozzles 114 may be formed in particular as full-jet nozzles and/or as flat-jet nozzles. It has been found that a good cleaning effect can be achieved with such nozzles if they are operated with a fluid pressure of approximately 3 bar. However, nozzle lances, which have multiple nozzles formed by bores on the outer circumference of a lance, may also be used in the chamber 104.

FIG. 2 is a schematic sectional view of the apparatus 100. The apparatus 100 contains an air filter 122. The filter 122 is preferably designed as a so-called "HEPA fine filter" with the special features mentioned hereafter. The air filter 122 acts as a suspended-matter filter. It preferably has a filter fineness of approximately 10 µm or less. The filter fineness specifies the particle size from which particles are retained by the filter.

For the filtering of air, the air filter 122 comprises in particular glass fiber mats with glass fibers of which the fiber diameter preferably lies in the range between 1 µm and 10 µm. Such glass fiber mats are fixed in a support frame and form there a corrugated or serrated filter structure. By means of the glass fiber mats, the air flowing through the air filter 122 is cleaned by a screening effect. This means that dirt particles in the air flowing through the air filter 122 remain trapped between the fibers of the glass fiber mats on account of their size. In addition, the air is also cleaned in the air filter 122 by inertial effects. This is so because the dirt particles in the air that passes through the filter 122 do not necessarily follow an air stream around the individual glass fibers in the glass fiber mats. On account of inertia, some dirt particles also impact corresponding glass fibers in the glass fiber mats. Such dirt particles then remain firmly attached to the glass fibers. The air flowing through the air filter 122 is additionally also cleaned by the so-called barrier effect. The barrier effect is based on the principle that very small dirt particles are attracted by glass fibers when they come very close to glass fibers in the air filter. Furthermore, the air in the air filter 122 is cleaned by diffusion effects. This is so because very small dirt particles do not move in the air filter 122 with the flow of an air stream but have any trajectory corresponding to Brownian molecular motion. If this Brownian motion of the dirt particles leads to collisions with glass fibers, these dirt particles likewise remain attached to the corresponding fibers.

The air filter 122 conforms to filter class H 10 according to European standard EN 1822-1:1998. For a particularly precise analysis of the soiling of workpieces, it is favorable to use as the filter a HEPA filter of which the air filter fineness is approximately 5 µm or less. The rinsing liquid 162 acts in this case as an extraction liquid for the dirt particles 178.

The apparatus 100 comprises a fan 124, by means of which air is passed through an intake device 126 over the fine filter 122 through channels 123 in a ceiling 128 in the chamber 104. The fan 124 makes it possible to set a positive-pressure atmosphere of filtered air in the chamber 104. This measure ensures that a clean-room atmosphere conforming to clean room class 3 as specified by ISO 14644 or clean room class 100 as specified by US Federal Standard 2009 can be set in the chamber 104. It ensures in particular that no dirt particles and liquid droplets can penetrate into the chamber 104 from the ambient air.

By means of the spray nozzles 114, dirt particles 178 on a workpiece 102 arranged, in the chamber 104 can be rinsed off with rinsing liquid 162. The rinsing liquid 162 thus acts as extraction liquid for the dirt particles 178 on a workpiece 102. The chamber 104 has walls 117 and a funnel-shaped floor 136 with rounded corners 137. The walls 117 are splash guard walls. The rounded corners 137 have the effect that no pockets of dirt can occur in the chamber 104. The floor 136 contains a drain opening 138. The drain opening 138 opens out into a pipeline 140.

In order to clean the walls 117 of the chamber 104, the apparatus 100 contains a wall rinsing device 115. The wall rinsing device 115 is connected to the pipeline 136 by means of a control valve 119.

The apparatus 100 contains a movable filter belt 146. The filter belt 146 consists of nonwoven filter fabric. It is moved in the apparatus 100 in the direction of the arrow 148 from an unwinding roller 150 to a winding-up roller 151. The unwinding roller 150 is an unwinding station, the winding-up roller 151 is a winding-up station. For the moving of the filter belt 146, the winding-up roller 151 is assigned an electric motor 154. The filter belt 146 is guided on the end flange 144 of the pipeline 140.

A funnel element 158 is arranged on the side 156 of the filter belt 146 that is facing away from the end flange 144. The funnel element 158 is connected to the system of lines 182 for rinsing liquid. The portion 168 of the filter belt 146 at the funnel element 158 acts as a retaining means in the form of a filter for dirt particles 178 from the workpiece 102. The funnel-shaped floor 136 of the chamber 104, the drain opening 138, the pipeline 140, the portion 168 and the funnel element 158 form a collecting device 142, in which the portion 168 is a retaining means for rinsed-off dirt particles 178.

By means of the electric motor 154, the portion 168 can be moved to a heating device 180 and on to a measuring device 170 with a microscope 171 by rolling up filter belt 146 on a winding-up roller 151. The heating device 180 serves for drying a portion 168 of the filter belt 146 before it is guided to the microscope 171. This makes it possible to view the dirt particles 178 rinsed off from a workpiece 102 by means of the microscope 171 without disturbing liquid droplets. The filter belt 146 with the unwinding roller 150 and the winding-up roller 151 acts as a transporting device 152 for the portion 168.

A suction pump 160 is arranged in the system of lines 182 for rinsing liquid. By means of the suction pump 160, rinsing liquid 162 can be sucked in through the portion 168 of the filter belt 146 in the region of the funnel element 158 and transported to a storage tank 164 for rinsing liquid. The system of lines 182 for rinsing liquid contains a feed pump 166. By means of the feed pump 166, the rinsing liquid can be pumped out of the storage tank 164 to the nozzles 114, in order to rinse off a workpiece arranged in the rinsing zone 120 with the rinsing liquid 162.

The microscope 171 in the measuring device 170 contains a digital image sensor 172. The digital image sensor 172 is connected to a computer unit 174. The computer unit 174 is an analyzing device. It has a program memory 176, in which an image processing program is loaded. By means of the image processing program, the number of dirt particles 178 captured in the portion 158 of the filter belt 146 and their characteristic parameter, for example their length, can be determined and documented. The number of dirt particles or their characteristic parameter is a measure of the soiling of a workpiece. With the computer unit 174, the degree of soiling of an individual workpiece can consequently be determined by comparison with a reference value.

For indicating the degree of soiling of a workpiece 102 determined by means of the measuring device 170, the apparatus has a display unit 173, which is shown in FIG. 1.

The apparatus described on the basis of FIGS. 1 and 2 for analyzing the soiling of workpieces is operated as will now be explained.

Firstly, the chamber 104 itself is rinsed with cleaning or extraction liquid 162 by the wall rinsing device 115, in order to remove from the arrangement dirt particles deposited on the walls 117 of the chamber 104. The rinsing liquid 162 is sucked in by means of the suction pump 160. Dirt particles 178 from the chamber 104 are thereby retained in the portion 168 of the filter belt 146.

By means of the electric motor 154, this portion 168 is then moved past the heating device 180 to the microscope 171. With the microscope 171 and the computer unit 174 assigned to the microscope 171, the degree of contamination of the chamber 104 is then determined. If the chamber 104 satisfies a cleanliness criterion fixed in advance and stored in the computer unit 174, this is followed for example by a workpiece 102 of which the degree of soiling is intended to be determined being arranged in the chamber 104 by an operator.

With the window 110 closed, the workpiece 102 is then rinsed off with rinsing liquid. If too many dirt particles are held in the portion 168, the procedure of rinsing the chamber 104 is possibly repeated. The rinsing liquid is moved through the filter belt 146 by means of the suction pump 160 through the suction opening 138. After the rinsing off of the workpiece, the filter belt 146 is moved first to the heating device 180 and then to the measuring device 170, in order to analyze the dirt particles 178 from the workpiece 102 retained in the portion 168 of the filter belt 146 by means of the microscope 171. If the soiling detected by the measuring device 170 thereby exceeds a threshold value, a warning message is issued on the display unit 173 of the apparatus 100.

Figure 3:
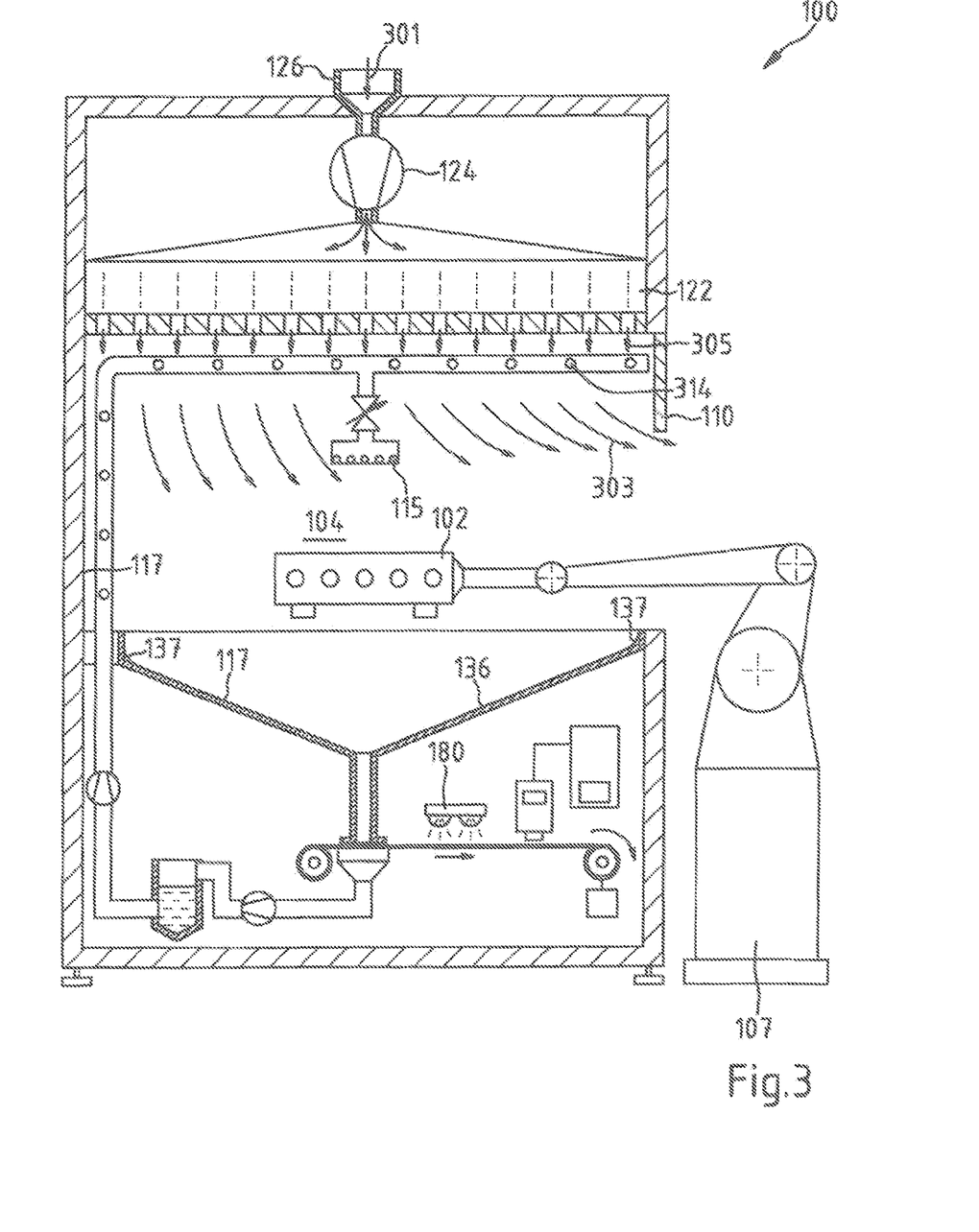
FIG. 3 shows a sectional view of the first apparatus with a handling robot.

FIG. 3 shows the apparatus 100 for analyzing the soiling of workpieces having a handling device 107 formed as a robot. Then no operator is required for the loading and unloading of the chamber 104 with a workpiece 102. In order that no dirt particles can penetrate into the open chamber 104 from the ambient air, an air stream 301 is thereby sucked in by means of the fan 124, and an air stream 303 flowing out of the chamber 104 to the outside through the air filter 122 and the channels 123 is set.

On the basis of the warning message, it may then be the case for example that the measuring of the soiling of the workpiece 102 is repeated. This is so because, when measuring the soiling in the apparatus 100, the workpiece is also cleaned. On the basis of the warning message, it may however then also be the case for example that production in an industrial production facility is interrupted.

FIG. 1 shows a further apparatus 400 for determining and analyzing the soiling of workpieces. To the extent to which the structure of the apparatus 400 corresponds to the structure of the apparatus 100 from FIGS. 1 and 2, subassemblies are identified in FIG. 4 by reference numerals increased by the number 300 in comparison with FIGS. 1 and 2.

Figure 4:
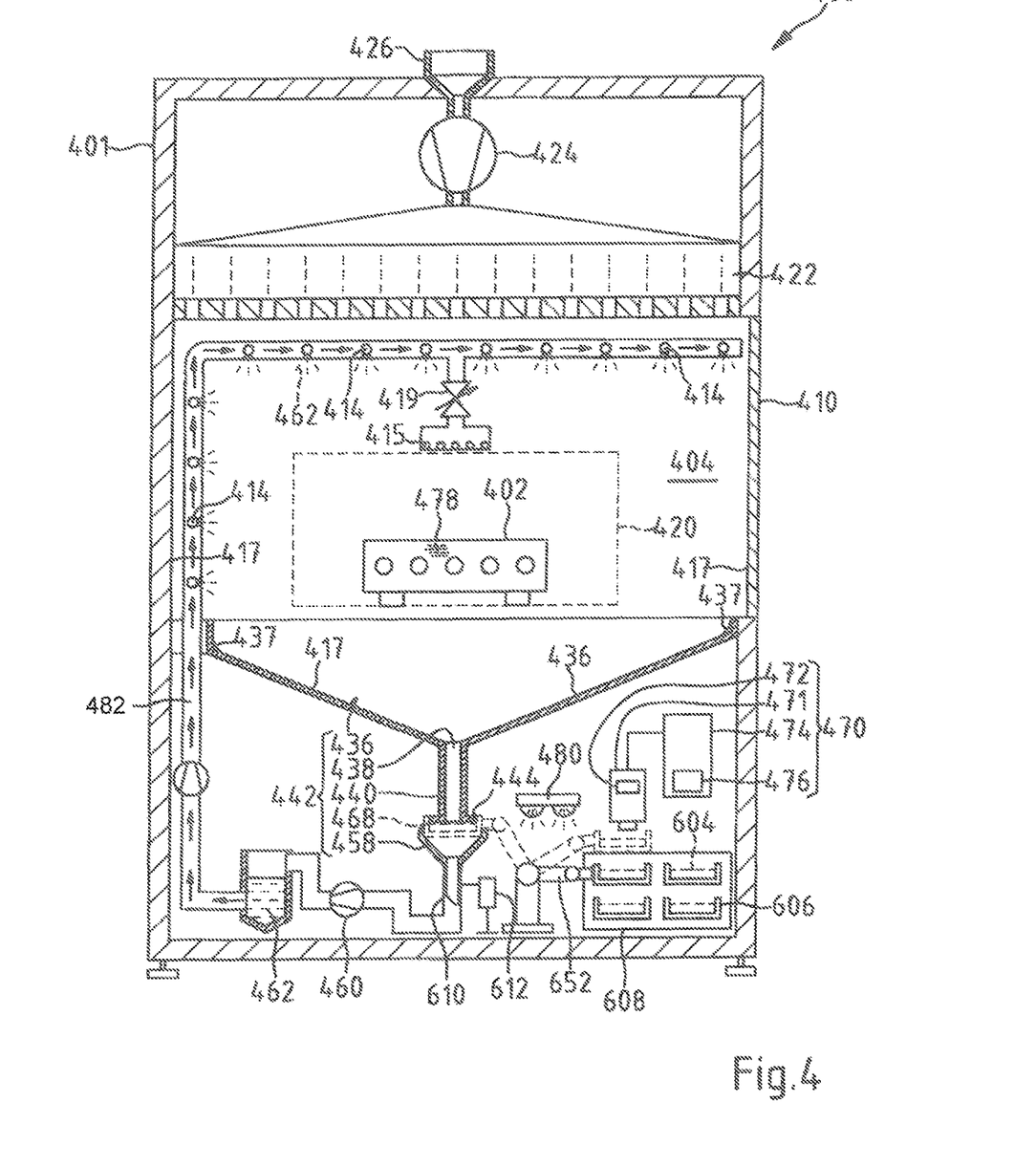
FIG. 4 shows a second apparatus for determining the soiling of workpieces with a collecting device for dirt particles and a measuring device; and, FIG. 5 and FIG. 6 show the collecting device of the second apparatus in different operating positions.

The apparatus 400 has a manipulator 652. The manipulator 652 is a handling robot. It serves the purpose of receiving from the magazine 608 a filter element 604 in the form of a filter membrane, which is arranged in a filter holder 606, in order to position it against the end flange 444 of the pipeline 440.

The filter element 604 is located in the filter holder 606 in a clamping ring (not shown). The clamping ring ensures that fluid interspersed with dirt particles in the filter holder 605 cannot move past the filter element 604.

In the apparatus 400, the funnel element 458 is arranged on a telescopic tube 610. The funnel element 458 can be moved in this telescopic tube 610 between a filtering position and a release position by means of a drive cylinder 612. Here, the funnel-shaped floor 436 of the chamber 404, the drain opening 438, the pipeline 440, the filter holder 606 with the filter membrane 604 as well as the funnel element 458 act as a collecting device 442, in which the filter membrane 604 is a retaining means for dirt particles 478. The manipulator 652 is a transporting device for this retaining means.

Figure 5:
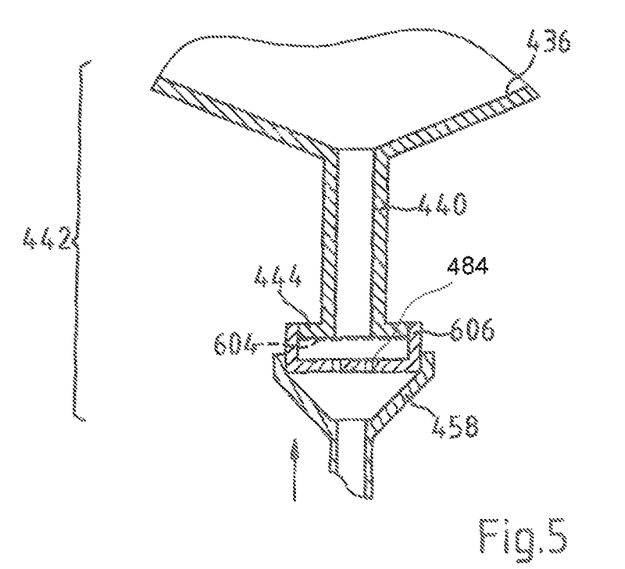

FIG. 5 shows the pipeline 440 and the funnel element 458 in the filtering position. In this position, rinsing liquid 462 can be sucked in from the chamber 404 through the filter element 604 in the filter holder 606 by means of the suction pump 460 in the system of lines 482. The filter holder 606 has openings 484 in the base thereof to allow the rinsing fluid to pass therethrough to the system of lines 482.

Figure 6:
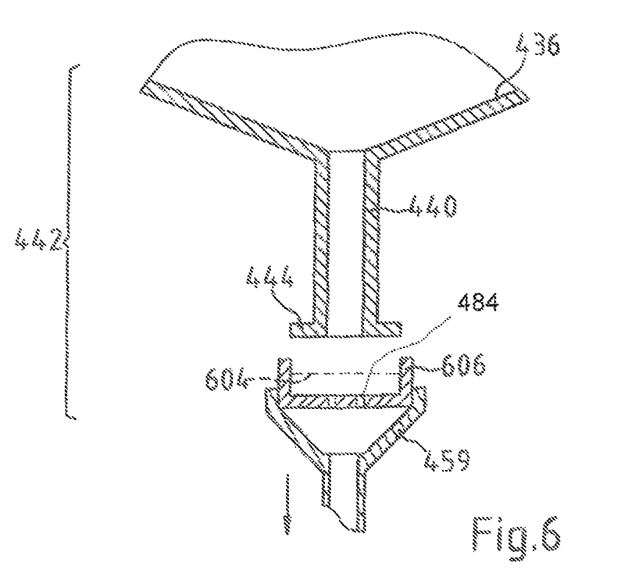

FIG. 6 shows the pipeline 440 and the filter element 604 in the release position. From the release position, the filter holder 606 with the filter element 604 can be moved by means of the manipulator 652 to the heating device 480 and from the heating device 480 under the microscope 471 of the measuring device 470.

In the measuring device 470, the dirt particles 478 collected in a filter element 604 are measured. The result of the measurement is then displayed on a display unit of the apparatus. Alternatively or in addition, the result of the measurement may also be transmitted to the control center of an industrial production plant.

After the measurement, the filter holder 606 with the filter element 604 is moved back into the magazine 608. For a new measurement, the manipulator 652 then removes from the magazine 608 a new filter holder 606 with an unused filter element 604 and moves it to the end flange 444 of the pipeline 440.

It is possible to rinse the walls 417 of the chamber 404 in the apparatus 400 with fluid from the wall rinsing device 415, even without a filter element 504 being arranged at the end flange of the pipeline 440. If the chamber 404 is rinsed without a workpiece, but with a filter element 604 arranged at the pipeline 440, it is possible to determine a blind value for dirt particles in the apparatus 400.

The automated apparatuses described above for analyzing the soiling of work-pieces are suitable in particular for integration in a production or assembly line, in order to realize an automatic cleanliness analysis there. Cleanliness analysis is meaningful in a production or assembly line particularly where a pre-assembly or final assembly of workpieces takes place. Here it is possible, for example in a production process, for workpieces to be examined at regular intervals in the manner of random sampling. This makes it possible, for example, to transmit an automatic batch record to a master control computer in a production plant. Cleanliness analysis before the pre-assembly and final assembly of workpieces ensures that no assembly of soiled workpieces takes place. Consequently, the invention also relates to an assembly line for the pre-assembly or final assembly of complex systems comprising multiple components, using an analyzing apparatus described above.

To sum up, the following preferred features of the invention are noted in particular: The invention relates to an apparatus (100, 400) for determining soiling of objects, in particular of workpieces. The apparatus (100, 400) has a rinsing zone (120, 420) for rinsing off dirt particles (178, 478) built up on an individual object (102, 402) by means of a fluid. The apparatus (100, 400) contains a collecting device (142, 442), which has at least one retaining means (168, 604) for capturing the dirt particles (178, 478) rinsed off from the individual object (102, 402). The apparatus (100, 400) comprises a transporting device (152, 652) for moving the dirt particles (178, 478) from the individual object (102, 402) that are captured by the at least one retaining means (168, 604) to a measuring device (170, 470). The measuring device (170, 470) serves for measuring at least one physical parameter of the dirt particles (178, 478) rinsed off from the individual object (102, 402).

It is understood that the foregoing description is that of the preferred embodiments of the invention and that various changes and modifications may be made thereto without departing from the spirit and scope of the invention as defined in the appended claims.

What is claimed is:

1. An apparatus for determining soiling of an object, the apparatus comprising:
    a rinsing zone for rinsing off dirt particles built up on an individual object with a fluid causing said fluid to entrain the rinsed off dirt particles;
    a collecting arrangement including a retaining device for capturing and retaining the dirt particles from said fluid at a first location;
    a measuring device disposed at a second location for measuring at least one physical parameter of the captured dirt particles; and
    a transport system for moving said retaining device with the dirt particles captured and retained thereon from said first location to said measuring device at said second location to permit measuring said physical parameter of the captured dirt particles.

2. The apparatus of claim 1, wherein said measuring device is configured to obtain measurement data as to the dirt particles rinsed from said object; and said measuring device includes an analyzing unit wherein the degree of soiling of said object is determined from said measurement data.

3. The apparatus of claim 1, wherein said retaining device includes a filter membrane; and a membrane holder for accommodating said filter membrane therein.

4. The apparatus of claim 3, wherein said transport system includes: a magazine for accommodating said membrane holder; and an automatically controlled manipulator configured to move said membrane holder from said magazine into said collecting arrangement and/or from said collecting arrangement into said measuring device.

5. The apparatus of claim 4, wherein said automatically controlled manipulator is a robot.

6. The apparatus of claim 1, further comprising a line system for circulating said fluid for rinsing off dirt particles in said rinsing zone; and said line system including at least one nozzle for rinsing off with said fluid in said rinsing zone.

7. The apparatus of claim 6, wherein said line system further includes a suction device for sucking said fluid with dirt particles entrained therein through said retaining device.

8. The apparatus of claim 7, further comprising a chamber surrounding said rinsing zone; and a device for setting an overpressure in said rinsing zone and/or for rinsing said rinsing zone by supplying a gaseous fluid, which has been freed of dirt particles, into said chamber.

9. The apparatus of claim 8, further comprising a filter through which said fluid, which is supplied to said chamber, is conducted so as to free said fluid of dirt particles.

10. The apparatus of claim 9, wherein said filter comprises glass fiber mats disposed in a corrugated or a serrated manner.

11. The apparatus of claim 8, further comprising a device mounted in said chamber for rinsing a wall of said chamber with fluid.

12. The apparatus of claim 1, further comprising a transport cabinet for accommodating said rinsing zone with said collecting arrangement and said measuring device therein.

13. The apparatus of claim 1, wherein said object is a workpiece.

14. An apparatus for determining soiling of an object, the apparatus comprising:
    a rinsing zone for rinsing off dirt particles built up on an individual object with a fluid;
    a collecting arrangement including a retaining device for capturing the dirt particles rinsed off from said individual object;

a measuring device for measuring at least one physical parameter of the captured dirt particles;

a transport system for moving the dirt particles captured with said retaining device to said measuring device to permit measuring said physical parameter of the captured dirt particles;

said measuring device being configured to obtain measurement data as to the dirt particles rinsed from said object;

said measuring device including an analyzing unit wherein the degree of soiling of said object is determined from said measurement data; and said transport system being configured to move said retaining device from said collecting arrangement to said measuring device.

15. An apparatus for determining soiling of an object, the apparatus comprising:

a rinsing zone for rinsing off dirt particles built up on an individual object with a fluid;

a collecting arrangement including a retaining device for capturing the dirt particles rinsed off from said individual object;

a measuring device for measuring at least one physical parameter of the captured dirt particles;

a transport system for moving the dirt particles captured with said retaining device to said measuring device to permit measuring said physical parameter of the captured dirt particles; and said transport system including a filter belt and said retaining device including a section of said filter belt.

16. The apparatus of claim 15, wherein said transport system further includes an unwinding station and a winding-up station for moving said filter belt out of said unwinding station to said winding-up station so as to cause said filter belt to function as a transport device for said section of said filter belt.

17. An apparatus for determining soiling of an object, the apparatus comprising:

a rinsing zone for rinsing off dirt particles built up on an individual object with a fluid;

a collecting arrangement including a retaining device for capturing the dirt particles rinsed off from said individual object;

a measuring device for measuring at least one physical parameter of the captured dirt particles;

a transport system for moving the dirt particles captured with said retaining device to said measuring device to permit measuring said physical parameter of the captured dirt particles; and said measuring device including a microscope having a digital camera and an evaluation computer.

* * * * *

UNITED STATES PATENT AND TRADEMARK OFFICE
CERTIFICATE OF CORRECTION

Page 1 of 1

PATENT NO. : 9,823,175 B2
APPLICATION NO. : 13/857005
DATED : November 21, 2017
INVENTOR(S) : H. David et al.

It is certified that error appears in the above-identified patent and that said Letters Patent is hereby corrected as shown below:

In the Specification

In Column 4:
Line 51: delete "," after "arranged".

In Column 5:
Line 44: delete "158" and substitute -- 168 -- therefor.

In Column 6:
Line 37: delete "FIG. 1" and substitute -- FIG. 4 -- therefor.

In Column 7:
Line 24: delete "504" and substitute -- 604 -- therefor.

Signed and Sealed this
Thirteenth Day of March, 2018

Andrei Iancu
*Director of the United States Patent and Trademark Office*